United States Patent [19]

Bobo, Jr.

[11] Patent Number: 4,648,869

[45] Date of Patent: Mar. 10, 1987

[54] AUTOMATIC INFILTRATION DETECTION SYSTEM AND METHOD

[75] Inventor: Donald E. Bobo, Jr., Irvine, Calif.

[73] Assignee: American Hospital Supply Corporation, Deerfield, Ill.

[21] Appl. No.: 804,675

[22] Filed: Dec. 4, 1985

[51] Int. Cl.⁴ ............................................... A61M 5/00
[52] U.S. Cl. ........................................ 604/49; 604/67; 604/118; 604/246; 128/DIG. 13
[58] Field of Search ............... 604/67, 50, 65, 66, 604/118, 245, 246; 128/DIG. 12, DIG. 13

[56] References Cited

U.S. PATENT DOCUMENTS

| | | | |
|---|---|---|---|
| 3,690,318 | 9/1972 | Gorsuch | 604/141 |
| 4,192,319 | 3/1980 | Hargens et al. | |
| 4,209,023 | 6/1980 | Layton | |
| 4,277,227 | 7/1981 | Jenkins | |
| 4,392,847 | 7/1983 | Whitney | 604/118 |
| 4,395,259 | 7/1983 | Prestele et al. | |
| 4,457,751 | 7/1984 | Rodler | |
| 4,468,219 | 8/1984 | George et al. | 604/66 |
| 4,534,756 | 8/1985 | Nelson | |

FOREIGN PATENT DOCUMENTS 1170528 7/1984 Canada .

OTHER PUBLICATIONS

"Interstitial Fluid Pressure In Muscle And Compartment Syndroms In Man", Alan R. Hargens et al, *Microvascular Research*, vol. 14, Academic Press 1977, pp. 1–10.

*Primary Examiner*—Stephen C. Pellegrino
*Attorney, Agent, or Firm*—Gordon L. Peterson

[57] ABSTRACT

An infusion system for infusing a flowable material into a patient comprising an infusion device for delivering the flowable material in both a normal delivery pattern and a test pulse and a conduit for conducting the flowable material from the infusion device to the patient. The test pulse creates a pressure wave response in the conduit. The pressure wave response is monitored and used to detect if the infiltration has occurred.

21 Claims, 6 Drawing Figures

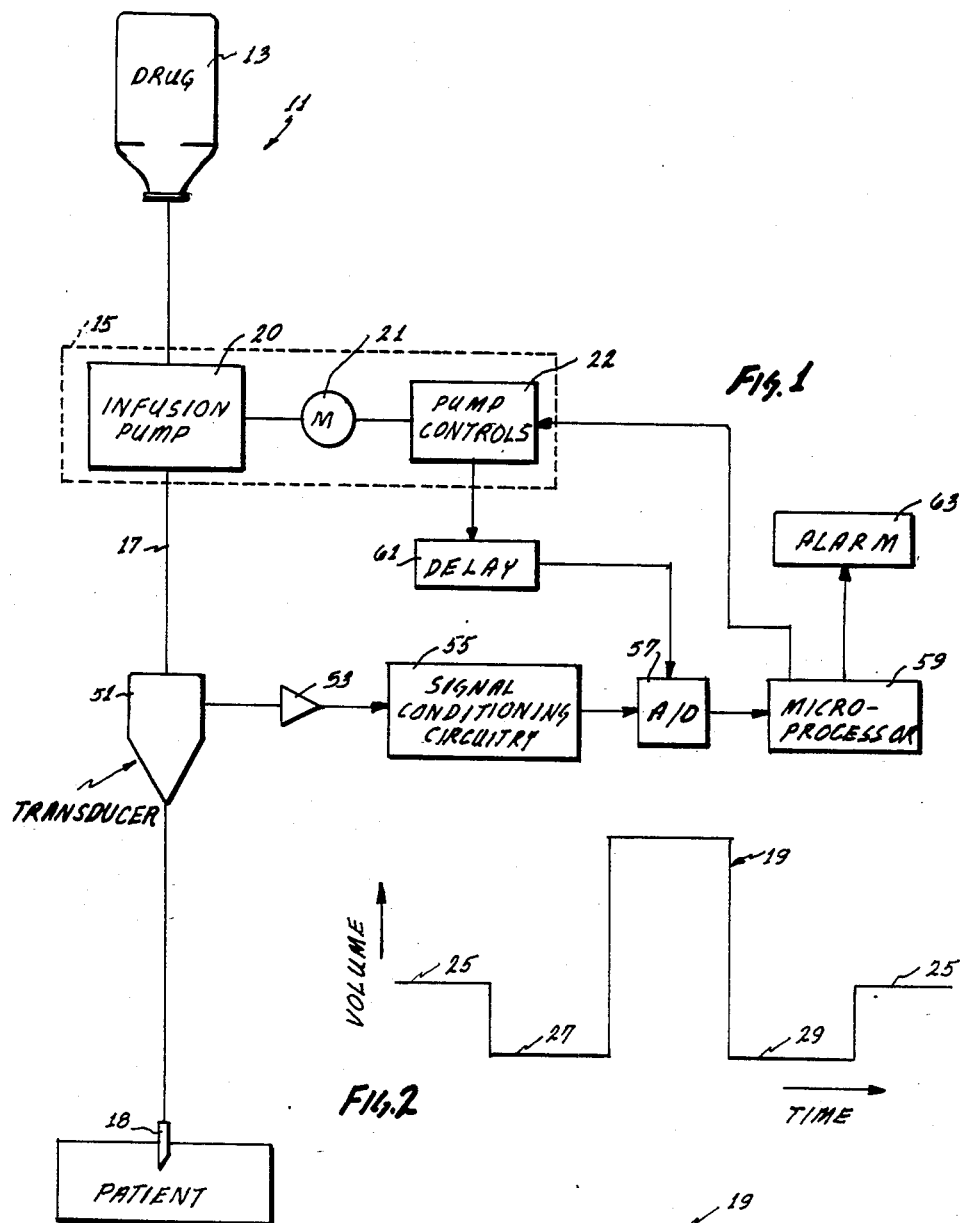
Fig. 1
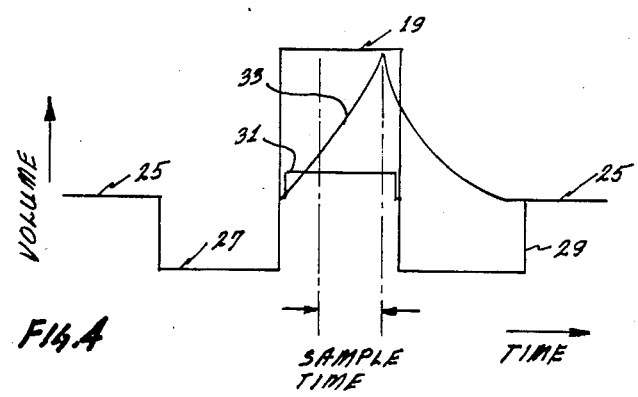
Fig. 2
Fig. 4

AUTOMATIC INFILTRATION DETECTION SYSTEM AND METHOD

BACKGROUND OF THE INVENTION

It is often necessary or desirable to infuse a flowable material, which may be liquid, a gas or a combination thereof, into a patient. One example is the administration of parenteral fluids to a patient.

A typical infusion system includes an infusion device for delivering flowable material and conduit means for conducting the flowable material from the infusion device to the patient. The conduit means typically comprises flexible tubing leading from the infusion device and a needle for insertion into the vascular system of the patient. In normal operation, the infusion device delivers the flowable material through the tubing and the needle to the vascular system of the patient.

One problem with infusion systems of this type occurs when the open distal end of the needle is not in communication with the interior of the vessel into which the flowable material is to be infused. This condition, which is known as infiltration, may occur, for example, when the needle is advanced through the vessel wall into tissue. In this event, the parenteral fluid will not be supplied to the interior of the vessel, and so the flowable material is improperly supplied by the conduit means to the patient. A similar problem may arise when attempting to infuse a flowable material into other regions of the body.

It is known to monitor the pressure of the flowable material delivered to the patient and to use the pressure information thus obtained for various control purposes. Examples of this are shown, by way of example, in Jenkins U.S. Pat. No. 4,277,227, Rodler U.S. Pat. No. 4,457,751 and Nelson U.S. Pat. No. 4,534,756. The system disclosed in the Nelson patent looks at different characteristics of the pressure being monitored depending upon the infusion flow rate to determine infiltration. For example, one characteristic is utilized for low flows and another characteristic is used for higher flows. This tends to complicate the infiltration detection apparatus. In addition, the system disclosed in this patent is limited to use with an infusion device whose normal delivery pattern or output is pulsed.

SUMMARY OF THE INVENTION

This invention provides a detection system and method which is usable with infusion devices regardless of the flow characteristics provided by the infusion device. For example, this invention can be used with an infusion device which has a normal delivery pattern with an essentially constant flow rate, i.e., a delivery pattern which has essentially no pulses. In addition, infiltration, or other condition indicative of the improper supply of flowable material to the patient, can be detected by monitoring the same characteristic of a pressure wave response regardless of the infusion rate, and this simplifies the infiltration detection system.

With this invention, the infusion device provides, or is controlled to provide, a test pulse of the flowable material with the test pulse being different from the normal delivery pattern of the infusion device. By way of example, the normal delivery pattern of the infusion device may be essentially constant or may have various other characteristics. The test pulse provides an increased flow rate of the flowable material for a relatively short duration, and this creates a pressure wave response in the conduit means leading from the infusion device to the patient. This pressure wave response, which exists regardless of the normal delivery pattern of the infusion device, is utilized to detect whether or not the flowable material is being improperly supplied by the conduit means to the patient. Although the improper supply could be due to various factors, such as an occlusion resulting from kinking of the tubing of the conduit means, in a more specific sense, the primary purpose of monitoring the pressure wave response is to detect infiltration.

To prevent the test pulse from altering the selected or programmed infusion rate, the infusion device may provide, or be programmed to provide, a reduced flow rate of the flowable material adjacent the test pulse. In a preferred arrangement, the reduced flow rate, and hence a reduced volume, is provided by delivery valleys or periods of reduced infusion rates on opposite sides of the test pulse, with the average flow rate through the valleys and test pulse equaling the selected infusion rate.

The infusion rate during the test pulse can advantageously be expressed as a function of the selected infusion rate, i.e., the desired infusion rate. With this invention, the infusion device includes means responsive to the selected infusion rate for controlling the infusion rate of the flowable material provided during the test pulse. More specifically, the ratio of the test pulse infusion rate to the selected infusion rate decreases as the selected infusion rate is increased. Of course, the test pulse may be provided automatically at known intervals and/or when demanded by an attendant.

The pressure wave response can be analyzed in various different ways to detect infiltration and other factors which are indicative of the flowable material being improperly supplied to the patient. Preferably, the rate of change of the pressure wave response is utilized and compared with a threshold magnitude. If the rate of pressure change exceeds the threshold magnitude, infiltration is indicated.

Another advantage of this invention is that the same characteristic of the pressure wave response can be utilized to determine infiltration regardless of the infusion rate. For example, the pressure wave response rises and then falls and has characteristics which change when the conduit means is not properly supplying the flowable material to the patient. This invention utilizes detection means which is responsive at all infusion rates of the infusion device to the change in pressure of the same portion of the pressure wave response during a predetermined period or sample time for detecting the improper supply of flowable material to the patient. Accordingly, it is not necessary to provide controls which can accommodate a switch-over to a different characteristic of the pressure wave response as the infusion flow rate is changed. Of course, the characteristic utilized at all infusion rates need not be the pressure change of the pressure wave response. For example, the selected characteristic could be or include an evaluation of the entire pressure wave response.

When infiltration or other improper supply of the flowable material to the patient is detected, various remedial action can be taken. For example, the infusion device may be shut off automatically and/or an alarm signal may be provided.

The invention, together with additional features and advantages thereof, may best be understood by reference to the following description taken in connection with the accompanying illustrative drawing.

BRIEF DESCRIPTION OF THE DRAWINGS

FIG. 1 is a block diagram illustrating one form of infusion system constructed in accordance with the teachings of this invention.

FIG. 2 is a plot of volume delivered by the infusion device versus time and illustrates a test pulse, two associated periods of reduced infusion rates, and regions of a normal delivery pattern.

FIG. 4 shows the two pressure wave responses of FIG. 3 in somewhat idealized form superimposed on the pump delivery plot of FIG. 2.

DESCRIPTION OF THE PREFERRED EMBODIMENT

Figure 3:
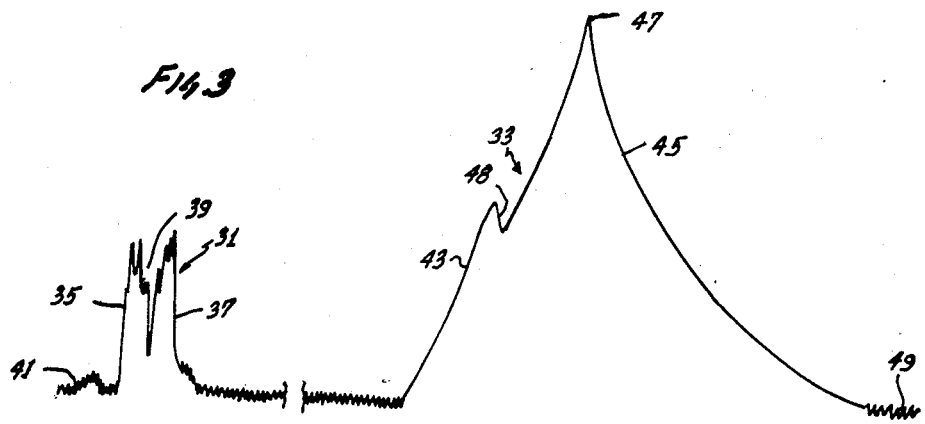
FIG. 3 is a plot showing one pressure wave response indicative of the flowable material being properly supplied to the vessel of a patient and a second pressure wave response indicative of infiltration.

FIG. 1 shows an infusion system 11 which comprises a source 13 of a parenteral fluid, an infusion device 15 for delivering the parenteral fluid through conduit means 17 to a patient. The conduit means 17 may comprise flexible tubing or other flow channels for supplying the parenteral fluid to the patient. The conduit means terminates in a needle 18, such as an I.V. needle, which is adapted to be inserted into a vessel of the patient's vascular system so that the open distal end of the needle communicates with the interior of the vessel. In this embodiment, the needle 18 is inserted into a vein. If the open distal end of the needle communicates with tissue, as when the needle is forced completely through the vessel wall, infiltration has occurred.

The infusion device 15 may be any infusion device which is controllable to produce a test pulse 19 (FIG. 2) and, as such, may include an infusion pump, a controller, syringe or the like. In this embodiment, the infusion device 15 includes a stepping motor 21 for driving the pump and pump controls 22 for controlling the stepping motor. The pump 20 is a positive displacement pump, and accordingly, its output can be controlled by controlling the speed of the motor 21. The pump controls 22 control the motor speed as described more fully hereinbelow to provide the infusion device with the desired output.

In a preferred construction, the infusion device 15 is a peristaltic pump of the type disclosed in application Ser. No. 661,032 entitled Continuous Delivery Peristaltic Pump and filed on Oct. 15, 1984. Such an infusion pump has a normal delivery pattern 25 which is essentially constant as shown by the flat portions of the pump delivery curve of FIG. 2. This is the result of accelerating through the deadband of the peristaltic pump. The curve of FIG. 2 is somewhat idealized in that the preferred infusion pump provides periodic short spikes and valleys of exceedingly short duration; however, these are sufficiently insignificant so that the normal delivery pattern of the pump can be considered as essentially constant.

Figure 5:
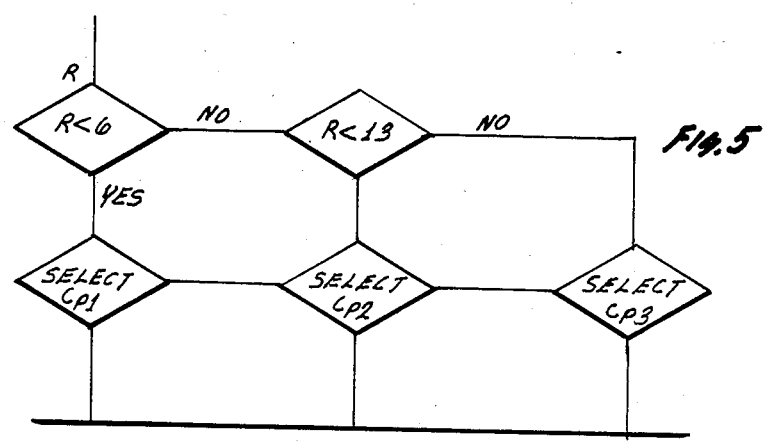
FIG. 5 is a flow chart showing one way that the flow rate during a test pulse can be selected as a function of selected infusion rate.

The pump controls 22 periodically, and/or on demand, increase the speed of the stepping motor 21 to cause the infusion pump 20 to provide the test pulse 19 which, in the illustrated embodiment of FIG. 2, is in the form of an essentially square wave having a duration of approximately four seconds. As described more fully hereinbelow with reference to FIGS. 5 and 6, the infusion rate, and hence the volume delivered, during the test pulse preferably varies with the selected infusion rate for the infusion device 15. However, the duration of the test pulse 19 may be constant for all selected infusion rates. Selection of the infusion rate also results in selection of the associated flow rate for the test pulse 19. In this regard, the pump controls 22, as is common for infusion devices of this type, are programmable to enable the attendant to select or punch in a desired or selected infusion rate.

The pump controls 22 reduce the speed of the stepping motor 21 just before and just after each test pulse 19 to cause the infusion pump 20 to provide infusion valleys 27 and 29 contiguous to, and on opposite sides of, the test pulse 19. The valleys 27 and 29 are square waves of short duration during which the infusion rate is reduced sufficiently to wholly or partially compensate for the increased infusion rate which takes place during the test pulse 19. Preferably, the valleys 27 and 29 reduce the total flow by the same amount that the test pulse increases it so that the average or net effect across the valleys 27 and 29 and the test pulse 19 is an infusion rate equal to the rate represented by the normal delivery pattern 25. For example, each of the valleys 27 and 29 may have a duration which is twice as long as the duration of the test pulse 19, with such duration being 8 seconds in this embodiment and constant for all selected infusion rates.

The presence of the test pulse 19 in the conduit means 17 creates a pressure wave response which has different characteristics depending upon whether or not the flowable material is being improperly supplied by the conduit means 17 to the patient. FIG. 3 shows examples of pressure wave responses 31 and 33 which indicate in-the-vessel and infiltration conditions, respectively. Although the pressure wave responses 31 and 33 are both shown in FIG. 3, they are not in scale in relation to each other.

The pressure provided by the pressure wave response 31 rises rapidly and almost instantaneously along a rising edge 35 and decays at about the same rate as represented by a falling edge 37. In between the edges 35 and 37, the pressure remains approximately constant, except for a short duration valley 39 which is representative of the deadband of the peristaltic pump being employed. In this regard, the pressure wave response 31 was generated by a peristaltic pump having a deadband and operating at about 350 cc's per hour, which is a high-delivery rate. If a peristaltic pump which accelerates through the deadband were employed, the duration and magnitude of the valley 39 would be greatly reduced. For this reason, it is preferred to utilize a peristaltic pump which does accelerate through the deadband so that any valley 39 would be of substantially less magnitude and duration than illustrated in FIG. 3. However, the pressure wave response 31 is essentially a square wave if the valley 39 is ignored. With the open distal end of the needle 18 of the conduit means 17 properly communicating with the interior of the vessel of the patient's cardiovascular system, the pressure wave response 31 is simply the result of forcing the additional flowable material into the fluid carried by the vessel. For example, for an infusion rate of 5 cc/hour, the pressure wave response 31 may rise about 5 mm Hg above a base line.

When infiltration occurs, the open distal end of the needle 18 is out of the interior of the vessel and communicates with tissue. As a result, the pressure wave response 33 is created in the conduit means 17. Specifically, the pressure wave response 33 rises along a rising edge 43 and falls along a falling edge 45 with both the rise time and fall time being much greater than for the pressure wave response 31. In addition, the pressure wave response 33 has a maximum pressure 47 which is much higher than the maximum pressure of the pressure wave response 31. For example, for an infusion rate of 5 cc/hour, the pressure wave response 33 may rise about 20 mm Hg above a baseline 49. The rising edge has a discontinuity 48 which is the result of using a peristaltic infusion pump to generate the pressure wave response 33 which did not accelerate through the deadband and, therefore, did not have an essentially constant delivery rate.

The pressure of the parenteral fluid in the conduit means 17 can be monitored in various different ways, such as by a pressure transducer 51 which provides an electronic analog pressure signal which is related to the pressure in the conduit means 17. This pressure signal can be processed in a variety of different ways to determine if the pressure wave response 31 is present. In this regard, any of a variety of different characteristics of the pressure wave response can be used to determine which of the two pressure wave responses is present in response to the test pulse 19. However, whichever characteristic is selected, the same characteristic may be used regardless of the infusion rate which the infusion device 15 is programmed to deliver.

Preferably, the rate of change of a portion of the pressure wave response is used to detect infiltration, and this can be best understood with reference to FIG. 4. FIG. 4 shows somewhat idealized pressure wave responses 31 and 33, which would be expected when using an infusion pump with an essentially constant output, superimposed on the delivery curve of the infusion device 15. Of course, the pressure wave responses 31 and 33 would not occur simultaneously as suggested by FIG. 4. As shown in FIG. 4, the portions of the pressure wave responses 31 and 33 which occur during a sample time are processed to determine which of the pressure wave responses is present. For example, during the sample time shown in FIG. 4, the pressure change along the pressure wave response 31 is essentially zero, whereas the pressure change from the beginning to the end of the sample time of the pressure wave response 33 is rather substantial. Accordingly, by determining the pressure change from the beginning to the end of the sample time and comparing this to a threshold magnitude, a decision can be made as to whether or not the pressure wave response 31 is present. The sample time may begin, for example, one second after the initiation of the test pulse and terminate, for example, one-half second before the end of the test pulse 19.

The change in pressure of the pressure wave response from the beginning to the end of the sample time can be determined in various ways, such as by integrating the pressure signal from the transducer 51 during the sample time and comparing the integral with a threshold magnitude in a comparator. However, in this embodiment, the pressure signal from the transducer 51 is amplified by an amplifier 53, conditioned in signal conditioning circuitry 55 and sampled in an analog-to-digital converter (A/D converter) 57 which provides the samples to a microprocessor 59. The signal conditioning circuitry 55 is conventional and is provided for the purpose of adjusting or compensating for various variables, such as temperature. Of course, if these variables are not considered significant, the signal conditioning circuitry 55 can be eliminated.

The samples of the pressure signal from the transducer 51 may be taken continuously or taken only during the sample time. In the former case, the microprocessor 59 is used to separate the samples taken during the sample time from those which are not. However, in this embodiment, the A/D converter 57 samples the pressure signal only during the sample time and provides the samples in a digital format to the microprocessor 59. The A/D converter 57 can be caused to sample the pressure signal during the sample time by transmitting a signal from the pump controls 22 to delay electronics 61 at the same instant that the pump controls 22 command the stepping motor 21 to reduce its speed to initiate the valley 27 which precedes the test pulse 19. The delay electronics 61 transmits this signal to the A/D converter 57 after a predetermined time delay which may be, for example, 9 seconds when the valley 27 is 8 seconds in duration and the test pulse 19 is 4 seconds in duration. This signal initiates operation of the A/D converter 57 for a predetermined time equal to the sample time so that samples of the pressure wave response are fed to the microprocessor 59 during the sample time.

The sampling frequency of the A/D converter 57 is preferably higher than the sampling frequency required for detecting infiltration. For example, if infiltration detection requires about one sample per second, samples may be taken at, for example, 5 samples per second. The 5 samples can then be combined in any of a variety of ways to produce an overall sample value for each second by the microprocessor 59. In any event, the microprocessor 59 ascertains the change in pressure from the beginning to the end of the sample time and compares the pressure change to a threshold magnitude of, for example, 8 mm Hg to determine if infiltration has occurred. If this pressure change exceeds 8 mm Hg, infiltration is detected. The threshold magnitude may be constant for all flow rates.

If the microprocessor 59 detects infiltration, it may initiate various remedial action. For example, it may provide a signal to an alarm 63 which provides an audio and/or visual alarm, and/or it may discontinue operation of the infusion device 15 by sending a stop signal to the pump controls to bring about discontinuing the transmission of signals to the stepping motor 21.

Another function of the pump controls 22 is to determine the infusion or flow rate during the test pulse 19. The infusion rate during the test pulse 19 is preferably a function of the selected infusion rate and may be expressed as a multiple of the selected infusion rate. Thus, as the attendant selects or punches in the selected infusion rate, the flow rate during the test pulse is simultaneously determined as a multiple of the selected infusion rate by software or logic circuitry in the pump controls 22. Because the valleys 27 and 29 represent known reductions in infusion rate, the depth of the valleys is simultaneously and automatically determined along with the infusion rate during the test pulse.

Figure 6:
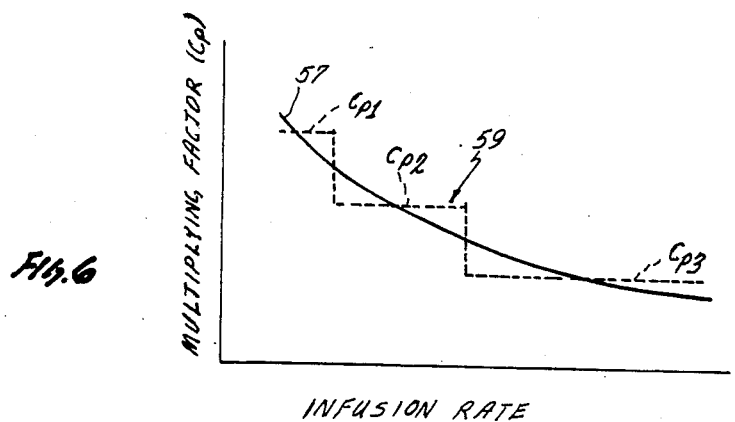
FIG. 6 is a plot of multiplying factor versus infusion rate.

The pump controls 22 can, of course, be programmed to vary infusion rate during the test pulse in any desired manner as a function of selected infusion rate. However, preferably, the infusion rate during the test pulse 19 equals the selected infusion rate times a multiplying factor, $C_p$. The multiplying factor $C_p$ and the ratio of test pulse flow rate to selected infusion rate reduce as selected infusion rate increases as shown by way of example in FIG. 6. For example, for a relatively low selected infusion rate, such as 2 cc's per hour, $C_p$ may equal 7. In other words, the infusion rate during the test pulse would be 7 times the infusion rate occurring during the normal delivery pattern 25 in FIG. 2. For a relatively high infusion rate, such as 100 cc's per hour, $C_p$ may equal a much lower number, such as 1.28. As shown in FIG. 6, the multiplying factor may be reduced along a smooth continuous curve 57 or in stepwise fashion along a curve 59 which is shown in dashed lines.

The presence of the valleys 27 and 29 is optional. However, for low infusion rates, the valleys are more desirable because increasing the infusion rate by a factor of "7" during the test pulse could represent a greater departure than desired from the selected infusion rate if the compensating effect of the valleys were eliminated. By way of contrast, at the higher infusion rates, where $C_p$ is a much lower number, the effect of the increased flow rate during the test pulse 19 might be regarded as too insignificant to warrant utilizing the offsetting effects of the valleys 27 and 29.

Although the pump controls 22 can implement virtually any desired equation for expressing $C_p$ as a function of the infusion rate, one suitable equation is as follows:

$$C = 1 + \frac{P_1 - P_2}{R}$$

where
$P_1$ is the pressure at the end of the sample time;
$P_2$ is the pressure at the beginning of the sample time; and
R is the selected infusion rate in cc/hour.

This equation could be implemented, for example, in several stages or steps by assuming values of $P_1-P_2$ for several different groups of flow rates as follows:

| $P_1 - P_2$ | Selected Infusion Rate |
|---|---|
| 12 | Up to 5 cc's per hour. |
| 20 | 6 to 12 cc's per hour. |
| 28 | over 12 cc's per hour. |

Of course, any number of steps can be used, and the three steps identified above are purely illustrative. This can be implemented, for example, with software as shown in the flow chart of FIG. 5 to obtain three different multiplying factors $C_{p1}$, $C_{p2}$ and $C_{p3}$ (FIGS. 5 and 6) which are applicable to the associated selected infusion rates (R).

Although an exemplary embodiment of the invention has been shown and described, many changes, modifications and substitutions may be made by one having ordinary skill in the art without necessarily departing from the spirit and scope of this invention.

I claim:
1. An infusion system for infusing a flowable material into a patient comprising:
   an infusion device for delivering the flowable material, said infusion device including means for delivering the flowable material in a normal delivery pattern and for delivering a test pulse of the flowable material with the test pulse being different from the normal delivery pattern and with the test pulse providing an increased flow rate of flowable material;
   conduit means for conducting the flowable material from the infusion device to the patient, said test pulse creating a pressure wave response in the conduit means; and
   means responsive to the pressure wave response in the conduit means for detecting if the flowable material is being improperly supplied by the conduit means to the patient.

2. An infusion system as defined in claim 1 wherein said normal delivery pattern has an essentially constant flow rate.

3. An infusion system as defined in claim 1 wherein said delivering means includes means for delivering a reduced flow rate of the flowable material adjacent the test pulse with said reduced flow rate being less than the flow rate during the normal delivery pattern to at least partially compensate for the increased flow rate of the flowable material provided during the test pulse.

4. An infusion system as defined in claim 3 wherein said reduced flow rate delivery means provides said reduced flow rates on opposite sides of the test pulse.

5. An infusion system as defined in claim 4 wherein the infusion device includes means for enabling the infusion device to selectively deliver the flowable material at different selected flow rates and means responsive to the selected flow rates for controlling the flow rate of the flowable material provided during the test pulse, and said controlling means decreases the ratio of test pulse flow rate to selected flow rate for increased selected flow rates and said detecting means includes means responsive to the rate of change of the pressure wave response in the conduit means for detecting infiltration.

6. An infusion system as defined in claim 1 wherein said delivering means includes means for enabling the infusion device to selectively deliver the flowable material at different selected flow rates and means responsive to the selected flow rate for controlling the flow rate of the flowable material provided during the test pulse.

7. An infusion system as defined in claim 6 wherein said controlling means decreases the ratio of test pulse flow rate to selected flow rate for increased selected flow rates.

8. An infusion system as defined in claim 1 wherein said delivering means includes means for selectively causing the infusion device to initiate a test pulse on demand.

9. An infusion system as defined in claim 1 wherein said detecting means includes means responsive to the rate of change of at least a portion of the pressure wave response in the conduit means for detecting if the flowable material is being improperly supplied by the conduit means to the patient.

10. An infusion system as defined in claim 1 wherein said detecting means detects the improper supply of the flowable material when the pressure change of at least a portion of the pressure wave response exceeds a predetermined magnitude.

11. An infusion system as defined in claim 1 wherein said detecting means includes a pressure transducer for providing a pressure signal which is related to the pressure in the conduit means, means for sampling said pressure signal at least during a sample time which occurs at least partially during the pressure wave response to provide a plurality of digital samples and means responsive to the samples obtained during said sample time for detecting if the flowable material is being improperly supplied by the conduit means to the patient.

12. An infusion system as defined in claim 1 wherein said detecting means is responsive at all infusion rates of the infusion device to the change in pressure of the same portion of the pressure wave response during a predetermined period for detecting if supply of the flowable material is being properly supplied to the patient.

13. An apparatus for use with an infusion device which infuses flowable material at any of a plurality of selected infusion rates through conduits means to a patient with the delivery of the flowable material from the infusion device including a pulse which provides a pressure wave response in the conduit means whose characteristics change depending upon whether or not the conduit means is properly supplying the flowable material to the patient, said apparatus comprising:

a pressure transducer for providing a pressure signal which is related to at least a portion of the pressure wave response;

means responsive to the same characteristic of the pressure wave response as represented by the pressure signal at all of said infusion rates for detecting if the flowable material is being properly supplied to the patient by the conduit means; and means responsive to the detecting means for providing remedial action if the flowable material is not being properly supplied to the patient.

14. An apparatus as defined in claim 13 wherein said characteristic is the change in pressure of the pressure wave response during a predetermined period.

15. A method for determining if a flowable material is being properly supplied to a patient by an infusion system, said method comprising:

delivering the flowable material through conduit means to a patient's vascular system in a normal delivery pattern and in a test pulse, with the test pulse being different from the normal delivery pattern and with the test pulse creating a pressure wave response in the conduit means; and monitoring at least a portion of the pressure wave response to detect if the flowable material is being improperly supplied by the conduit means to the patient.

16. A method as defined in claim 15 wherein said step of delivering the flowable material in a normal delivery pattern includes delivering the flowable material at an essentially constant flow rate.

17. A method as defined in claim 15 wherein said step of delivering includes delivering the flowable material at a reduced flow rate for a predetermined length of time to at least partially compensate for the increased flow rate of the flowable material provided during the test pulse.

18. A method as defined in claim 15 wherein said step of monitoring includes sensing the rate of change of the pressure of at least a portion of the pressure wave response and utilizing this information to detect infiltration.

19. A method as defined in claim 15 wherein said step of monitoring includes monitoring the same characteristic of the pressure wave response regardless of the flow rate of the flowable material during said normal delivery pattern.

20. A method for detecting infiltration wherein an infusion device infuses the flowable material at any of a plurality of selected infusion rates through a conduit means to a patient's vascular system with the delivery of the flowable material from the infusion device including a pulse which provides a pressure wave response in the conduit means whose characteristics change depending upon whether or not infiltration has occurred, said method comprising:

monitoring the same characteristic of the pressure wave response regardless of the infusion rates to detect if infiltration has occurred; and providing remedial action if infiltration is detected.

21. A method as defined in claim 20 wherein said characteristic is the change in pressure of a portion of the pressure wave response occurring during a predetermined period.

* * * * *